United States Patent [19]

Krüger et al.

[11] Patent Number: 4,695,563
[45] Date of Patent: Sep. 22, 1987

[54] ARTHROPODICIDAL PHOSPHORUS-CONTAINING HETEROCYCLES

[75] Inventors: Bernd-Wieland Krüger, Wuppertal; Wolfgang Behrenz, Overath; Benedikt Becker, Mettmann; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 870,043

[22] Filed: Jun. 3, 1986

[30] Foreign Application Priority Data

Jun. 7, 1985 [DE] Fed. Rep. of Germany ....... 3520388
Nov. 2, 1985 [DE] Fed. Rep. of Germany ....... 3538894

[51] Int. Cl.$^4$ .................. A01N 51/36; C07F 9/21
[52] U.S. Cl. .................................. 514/105; 558/83; 558/86
[58] Field of Search .............. 558/83, 86; 514/103, 514/105

[56] References Cited

U.S. PATENT DOCUMENTS 2,744,128 5/1956 Morris et al. ................ 558/86
3,773,711 11/1973 Dever et al. ................ 558/83

FOREIGN PATENT DOCUMENTS 1104520 10/1961 Fed. Rep. of Germany ........ 558/83
1926565 6/1973 Fed. Rep. of Germany .

OTHER PUBLICATIONS

Nikonova et al., "Bull. of Academy of Sciences of U.S.S.R.", vol. 29, (1980) pp. 663–668.

Primary Examiner—Anton H. Sutto
Attorney, Agent, or Firm—Sprung Horn Kramer & Woods

[57] ABSTRACT

Novel arthropodicidally active compounds of the formula

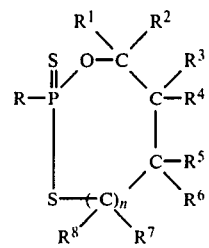

in which

R represents amino or optionally substituted radicals from the series comprising alkyl, alkylamino, methylalkylamino, alkoxy, alkenyloxy and alkylthio, $R^1$ to $R^8$ are identical or different and represent hydrogen or optionally halogen-substituted radicals from the series comprising alkyl, alkenyl, alkoxyalkyl and alkylthioalkyl, or represent halogen, nitro or dialkylaminoalkyl or represent optionally substituted phenyl or benzyl, and two of the radicals $R^1$ to $R^8$, together with the carbon atom or atoms to which they are bonded, may furthermore form an optionally substituted monocyclic or bicyclic ring, and n represents zero or 1.

intermediates therefor wherein R is replaced by Cl are also novel.

10 Claims, No Drawings

ARTHROPODICIDAL PHOSPHORUS-CONTAINING HETEROCYCLES

The invention relates to new substituted phosphorus-containing heterocycles, 1,3,2-oxathiaphosphorinane 2-sulphides and 1,3,2-oxathiaphosphapane 2-sulphides, several processes for their preparation and their use as pest-combating agents, preferably as arthropodicides, in particular as insecticides and acaricides and nematicides.

It is known that certain P-heterocycles, such as, for example, 5-membered cyclic thiophosphoramide diesters (M. Eto et al., J. Pesticide Sci., 3, 161 (1978)) or O,S esters of dithiophosphonic acid (see German Patent Specification No. 1,104,520) can be used as pest-combating agents.

However, the insecticidal and acaricidal action of the known compounds is not always satisfactory, particularly in the case of low active compound concentrations and application rates.

New P heterocycles of the general formula (I)

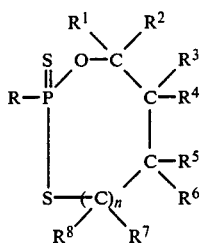

in which

R represents amino or optionally substituted radicals from the series comprising alkyl, alkylamino, methylalkylamino, alkoxy, alkenyloxy and alkylthio, $R^1$ to $R^5$ are identical or different and represent hydrogen or optionally hatogen-substituted radicals from the series comprising alkyl, alkenyl, alkoxy-alkyl and alkylthioalkyl, or represent halogen, nitro or dialkylaminoalkyl or represent optionally substituted phenyl or benzyl, and two of the radicals $R^1$ to $R^8$, together with the carbon atom or atoms to which they are bonded, may furthermore form an optionally substituted monocyclic or bicyclic ring, and n represents zero or 1, have been found.

The new compounds of the general formula (I) are obtained when (a) halides of the general formula (II)

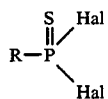

in which

Hal represents halogen, preferably chlorine or bromine, in particular chlorine, and R has the meaning given above, are reacted with compounds of the general formula (III)

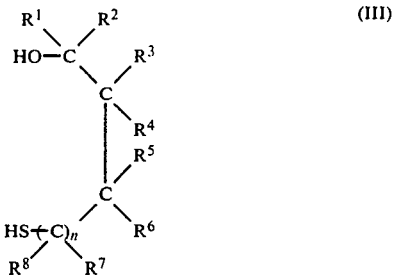

in which $R^1$ to $R^8$ and n have the abovementioned meaning, if appropriate in the presence of an acid acceptor and, if appropriate, in the presence of diluents, or (b) dithioanhydrides of the general formula (IV)

in which R represents optionally substituted alkyl, are reacted with alcohols of the general formula (V)

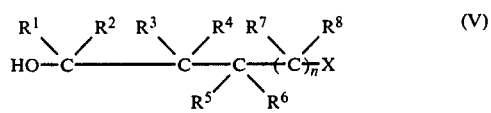

in which $R^1$ to $R^8$ and n have the abovementioned meaning and x represents halogen, preferably chlorine or bromine, in particular chlorine, or represents a sulphonate radical of the general formula (VI)

in which Y represents optionally substituted alkyl or aryl, if appropriate using a diluent and, if appropriate, with the addition of an acid acceptor, or (c) first (analogously to method a) thiophosphoryl trichloride ($PSCL_3$) is reacted with compounds of the general formula (III) to give 2-chloro-1,3,2-oxathia-P-cycles of the general formula (VII)

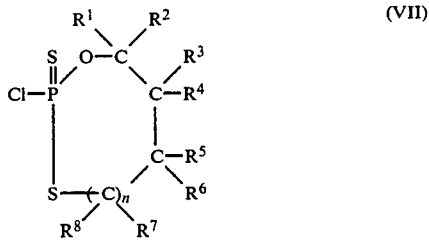

in which $R^1$ to $R^8$ and n have the abovementioned meaning, and, if appropriate after they have been isolated, these compounds are then reacted, in a second reaction step, with a compound of the general formula (VIII)

in which

R has the abovementioned meaning, with the exception of optionally substituted alkyl, and M represents hydrogen or one equivalent of an alkali metal or alkaline earth metal ion (such as sodium, potassium or calcium) or an ammonium ion, if appropriate in the presence of acid acceptors and, if appropriate, in the presence of diluents.

The new P-heterocycles of the general formula (1) are distinguished by a high activity against animal pests, preferably against metropods in particular by a high insecticidal and acaricidal activity as well as a nematicidal activity. They can also be used in synergistic mixtures with other pest-combating agents.

Surprisingly, the compounds according to the invention, of the general formula (I), exhibit a substantially higher insecticidal and acaricidal and nematicidal action than corresponding known compounds.

The radicals given in the general formulae preferably have the following meaning:

The alkyl group in the alkylamino radical R and in the methyl-alkylamino radical R is straight-chain or branched and contains 1 to 8, preferably 1 to 6 and in particular 1 to 4, carbon atoms. Methyl, ethyl, n- and 1-propyl may be mentioned as examples.

The alkyl groups in the dialkylamino-alkyl radicals $R^1$ to $R^8$ are identical or different and straight-chain or branched, and preferably contain 1 to 6, in particular 1 to 4, carbon atoms. Methyl, ethyl and n- and i-propyl may be mentioned as examples.

In the dialkylamino-alkyl radicals $R^1$ to $R^8$, the alkyl groups to which the dialkylamino component is bonded preferably contains 1 to 6, in particular 1 to 4, carbon atoms.

Optionally substituted alkyl radicals R are straight-chain or branched alkyl preferably having 1 to 6, in particular 1 to 4, carbon atoms. Optionally substituted methyl, ethyl, n- and i-propyl, n-, i- and t.-butyl may be mentioned as examples.

Optionally substituted alkoxy radicals R are straight-chain or branched alkoxy preferably having 1 to 6, in particular 1 to 4, carbon atoms. Optionally substituted methoxy, ethoxy, n.- and i.-propoxy and n.-, i.- and t.-butoxy may be mentioned as examples.

Optionally substituted alkenyloxy radicals R are straight-chain or branched alkenyloxy preferably having 2 to 6, in particular 2 to 4, carbon atoms. Optionally substituted propenyloxy and butenyloxy may be mentioned as examples.

Optionally substituted alkylthio radicals R are straight-chain or branched alkylthio preferably having 1 to 6, in particular 1 to 4, carbon atoms. Optionally substituted methylthio, ethylthio, n.- and i.-propythio, n.-, i.- and t.-butylthio may be mentioned as examples.

In optionally halogen-substituted alkyl radicals $R^1$ to $R_8$, alkyl denotes straight-chain or branched alkyl preferably having 1 to 6, in particular 1 to 4, carbon atoms. Methyl, ethyl, n.- and i.-propyl, n.-, i.- and t.-butyl, each of which is optionally substituted by halogen, preferably fluorine, chlorine or bromine, may be mentioned as examples, and chloromethyl and bromomethyl should be particularly singled out.

Optionally halogen-substituted alkenyl radicals $R^1$ to $R^8$ are straight-chain or branched alkenyl preferably having 2 to 6, in particular 2 to 4, carbon atoms. Ethenyl, propen-1-yl, propen-2-yl and buten-3-yl, each of which is optionally substituted by halogen, preferably fluorine, chlorine or bromine, may be mentioned as examples.

The alkoxyalkyl and alkylthioalkyl radicals $R^1$ to $R^8$ which are optionally substituted by halogen (preferably fluorine, chlorine or bromine) preferably contain 2 to 8, in particular 2 to 6, carbon atoms. Halogen-substituted methoxymethyl, ethoxymethyl, methylthio-methyl, methylthioethyl and ethylthiomethyl may be mentioned as examples.

Two of the radicals $R^1$ to $R^8$, together with the carbon atom or atoms to which they are bonded, can form 5-membered to 7-membered cycloalkyl or cycloalkenyl rings which may additionally be bridged by a methylene or ethylene group and which can furthermore be substituted by one or two alkyl groups, preferably one alkyl group, preferably methyl or ethyl.

The optionally substituted radicals R and $R^1$ to $R^8$ can carry one or more, preferably 1 to 3, in particular 1 or 2, identical or different substituents. The following may be listed as examples of substituents: alkyl preferably having 1 to 4, in particular 1 or 2, carbon atoms, such as methyl, ethyl, n- and i-propl and n.-, i.- and t.-butyl; alkoxy preferably having 1 to 4, in particular 1 or 2, carbon atoms, such as methoxy, ethoxy, n.- and i.-propoxy and n.-, i.- and t.-butoxy; alkylthio preferably having 1 to 4, in particular 1 or 2, carbon atoms, such as methylthio, ethylthio, n.- and i.-propylthio and n.- and t.-butylthio; halogenoalkyl, preferably having 1 to 4, in particular 1 or 2, carbon atoms and preferably 1 to 5, in particular 1 to 3, halogen atoms, the halogen atoms being identical or different and being preferably fluorine, chlorine or bromine, in particular fluorine, such as trifluoromethyl; halogen, preferably fluorine, chlorine, bromine and iodine, in particular chlorine and bromine; cyano; nitro; carbamoyl; alkylcarbonyl preferably having 2 to 5 carbon atoms and alkoxycarbonyl preferably having 2 to 5 carbon atoms. Halogen, in particular chlorine and bromine, may be mentioned as preferred substituents.

Optionally substituted alkyl radicals Y are preferably alkyl which has 1 to 4 carbon atoms and is optionally substituted by halogen (fluorine, chlorine and/or bromine, preferably fluorine), methyl and trifluoromethyl being mentioned as examples.

Optionally substituted aryl radicals Y are preferably phenyl which is optionally substituted by alkyl having 1 to 4 carbon atoms, and 4-methylphenyl may be mentioned as an example.

Unless stated otherwise, halogen denotes fluorine, chlorine, bromine and iodine, preferably fluorine, chlorine and bromine, in particular chlorine and bromine.

Preferred compounds of the general formula (I) are those
in which
R represents amino, $C_1$–$C_6$-alkylamino, methyl-($C_1$–$C_6$-alkyl)-amino or optionally halogen-substituted $C_1$–$C_6$-alkyl, $C_2$–$C_6$-alkenyloxy, $C_1$–$C_6$-alkoxy or $C_1$–$C_6$-alkenyloxy, $R^1$ to $R^8$ are identical or different and represent hydrogen, halogen, $NO_2$, $C_1$–$C_6$-alkyl which can be halogen-substituted, $C_2$–$C_8$-alkenyl, di-($C_1$–$C_4$-alkyl)-amino, $C_1$–$C_4$-alkoxy-$C_1$–$C_4$-alkyl, $C_1$–$C_4$-alkykthio-$C_1$–$C_4$-alkyl, benzyl or phenyl, or in which
two of the radicals $R^1$ to $R^8$, together with the carbon atom or carbon atoms to which they are bonded, form a $C_5$–$C_7$-cycloalkyl or cycloalkenyl ring which can be substituted by methyl or ethyl and which can be bridged by a methylene or ethylene group to form a bicyclic ring, and n represents zero or 1.

Particularly preferred compounds of the general formula (I) are those
in which

R represents $C_1$-$C_4$-alkyl, $C_1$-$C_6$-alkoxy, $C_2$-$C_5$-alkenyloxy, $C_1$-$C_4$-alkylthio, $C_1$-$C_4$-alkylamino or methyl-($C_1$-$C_4$-alkyl)-amino, $R^1$ to $R^8$ are identical or different and represent hydrogen, nitro, or optionally halogen-substituted $C_1$-$C_4$-alkyl, or represents $C_1$-$C_4$-alkylthio-$C_1$-$C_4$-alkyl, or two of the radicals $R^1$ to $R^8$, together with the carbon atom or atoms to which they are bonded, form a 5-membered or 6-membered cycloalkyl or cycloalkenyl ring which can be bridged by a methylene or ethylene group to form a bicyclic ring, and n represents zero or 1.

Very particularly preferred compounds of the general formula (I) are those
in which R represents $C_1$-$C_4$-alkyl, $C_1$-$C_6$-alkoxy, $C_1$-$C_4$-alkylamino or methyl-($C_1$-$C_4$-alkyl)-amino, $R^1$ to $R_8$ are identical or different and represent hydrogen or $C_1$-$C_4$-alkyl which is optionally substituted by chlorine or bromine, and n represents zero or 1.

Compounds of the general formula (I) which are singled out as being very particularly preferred are those
in which R represents methyl, ethyl, methylamino, dimathylamino or methoxy.

$R^1$ to $R^8$ are identical or different and represent hydrogen, methyl, ethyl or n- or i-propyl, and n represents zero or 1.

The compounds of the formula (I) contain one or more centers of asymmetry and can therefore occur in the form of diastereomers or diastereomer mixtures.

The compounds of the general formula (VII) are new. They and the abovementioned process for their preparation form part of the present invention. The preferred meanings of the definitions of the radicals $R^1$ to $R^8$ correspond to the preferred meanings stated for the general formula (I).

If, for example, methanethiophosphonic dichloride and 3-hydroxy-propylmercaptan are used as starting materials for process variant (a), the reaction of these compounds can be represented by the following equation:

$$CH_3-\overset{\overset{S}{\|}}{P}Cl_2 + \begin{array}{c}HO-\\ \\HS-\end{array}\Big> \xrightarrow{-2HCl} CH_3-\overset{\overset{S}{\|}}{P}\overset{O-}{\underset{S-}{\Big>}}$$

If ethanethiophosphonic dithioanhydride and 4-chlorobutan-1-ol are used as starting materials for process variant (b), the reaction of these compounds can be represented by the following equation:

$$C_2H_5-\overset{\overset{S}{\|}}{P}\overset{S}{\underset{S}{\diagdown\diagup}}\overset{\overset{S}{\|}}{P}-C_2H_5 + 2\begin{array}{c}HO-\\ \\Cl-\end{array}\Big> \xrightarrow{-2HCl}$$

$$2C_2H_5-\overset{\overset{S}{\|}}{P}\overset{O-}{\underset{S-}{\Big>}}$$

If thiophosphoryl trichloride, 3-hydroxypropylmercaptan and sodium methylate are used as starting materials for process variant (c), the two-stage reaction of these compounds can be represented by the following equation:

$$S=PCl_3 + \begin{array}{c}HO-\\ \\HS-\end{array}\Big> \xrightarrow{-2HCl}$$

$$Cl-\overset{\overset{S}{\|}}{P}\overset{O-}{\underset{S-}{\Big>}} \xrightarrow[-NaCl]{+NaOCH_3} CH_3O-\overset{\overset{S}{\|}}{P}\overset{O-}{\underset{S-}{\Big>}}$$

The compounds of the general formulae (II), (III), (IV), (V), (VI) and (VIII) required as starting materials are generally known compounds of organic chemistry and can be prepared by known processes and methods.

The compounds of the formula (VII) which are required as starting materials are new. The preparation is carried out as described under process (c) (also see preparation examples).

The following may be mentioned as examples of the (VII)

$$Cl-\overset{\overset{S}{\|}}{\underset{S-(C)_n}{P}}\overset{O-C\overset{R^1}{\underset{R^2}{\diagup}}}{\underset{R^8\overset{}{\diagup}\underset{R^7}{\diagdown}}{\diagdown}}\overset{\underset{R^3}{\diagup}}{\underset{R^6}{C-R^4}}\overset{}{\underset{C-R^5}{|}}$$

| $R^1$ | $R^2$ | $R^3$ | $R^4$ | $R^5$ | $R^6$ | $R^7$ | $R^8$ |
|---|---|---|---|---|---|---|---|
| 1. n represents zero ||||||||
| H | H | H | H | H | H | | |
| CH$_3$ | H | H | H | H | H | | |
| H | H | CH$_3$ | H | H | H | | |
| H | H | H | H | CH$_3$ | H | | |
| C$_2$H$_5$ | H | H | H | H | H | | |
| H | H | C$_2$H$_5$ | H | H | H | | |
| H | H | H | H | C$_2$H$_5$ | H | | |
| n-C$_3$H$_7$ | H | H | H | H | H | | |
| H | H | n-C$_3$H$_7$ | H | H | H | | |
| H | H | H | H | n-C$_3$H$_7$ | H | | |
| i-C$_3$H$_7$ | H | H | H | H | H | | |
| H | H | i-C$_3$H$_7$ | H | H | H | | |
| H | H | H | H | i-C$_3$H$_7$ | H | | |
| t-C$_4$H$_9$ | H | H | H | H | H | | |
| H | H | t-C$_4$H$_9$ | H | H | H | | |
| H | H | H | H | t-C$_4$H$_9$ | H | | |
| CH$_3$ | CH$_3$ | H | H | H | H | | |
| CH$_3$ | C$_2$H$_5$ | H | H | H | H | | |
| CH$_3$ | n-C$_3$H$_7$ | H | H | H | H | | |
| CH$_3$ | i-C$_3$H$_7$ | H | H | H | H | | |
| C$_2$H$_5$ | C$_2$H$_5$ | H | H | H | H | | |
| C$_2$H$_5$ | n-C$_3$H$_7$ | H | H | H | H | | |
| C$_2$H$_5$ | i-C$_3$H$_7$ | H | H | H | H | | |
| n-C$_3$H$_7$ | i-C$_3$H$_7$ | H | H | H | H | | |
| H | H | CH$_3$ | CH$_3$ | H | H | | |
| H | H | CH$_3$ | C$_2$H$_5$ | H | H | | |
| H | H | CH$_3$ | C$_3$H$_7$ | H | H | | |

-continued

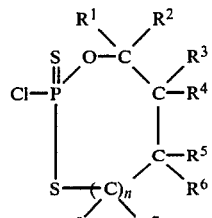

(VII)

| R¹ | R² | R³ | R⁴ | R⁵ | R⁶ | R⁷ | R⁸ |
|---|---|---|---|---|---|---|---|
| H | H | CH₃ | i-C₃H₇ | H | H | | |
| H | H | C₂H₅ | C₂H₅ | H | H | | |
| H | H | C₂H₅ | C₃H₇ | H | H | | |
| H | H | C₂H₅ | i-C₃H₇ | H | H | | |
| H | H | C₃H₇ | C₃H₇ | H | H | | |
| H | H | C₃H₇ | i-C₃H₇ | H | H | | |
| CH₃ | H | CH₃ | CH₃ | H | H | | |
| CH₃ | H | CH₃ | C₂H₅ | H | H | | |
| CH₃ | H | CH₃ | C₃H₇ | H | H | | |
| CH₃ | H | CH₃ | i-C₃H₇ | H | H | | |
| CH₃ | H | C₂H₅ | C₂H₅ | H | H | | |
| CH₃ | H | C₂H₅ | C₃H₇ | H | H | | |
| CH₃ | H | C₂H₅ | i-C₃H₇ | H | H | | |
| CH₃ | H | C₃H₇ | C₃H₇ | H | H | | |
| CH₃ | H | C₃H₇ | i-C₃H₇ | H | H | | |
| CH₃ | CH₃ | CH₃ | CH₃ | H | H | | |
| CH₃ | CH₃ | CH₃ | C₂H₅ | H | H | | |
| CH₃ | CH₃ | CH₃ | C₃H₇ | H | H | | |
| CH₃ | CH₃ | CH₃ | i-C₃H₇ | H | H | | |
| CH₃ | CH₃ | C₂H₅ | C₂H₅ | H | H | | |
| CH₃ | CH₃ | C₂H₅ | C₃H₇ | H | H | | |
| CH₃ | CH₃ | C₂H₅ | i-C₃H₇ | H | H | | |
| CH₃ | CH₃ | C₃H₇ | C₃H₇ | H | H | | |
| CH₃ | CH₃ | C₃H₇ | i-C₃H₇ | H | H | | |
| CH₃ | CH₃ | CH₃ | CH₃ | CH₃ | H | | |
| CH₃ | CH₃ | CH₃ | CH₃ | C₂H₅ | H | | |
| CH₃ | CH₃ | CH₃ | CH₃ | C₃H₇ | H | | |
| CH₃ | CH₃ | CH₃ | CH₃ | i-C₃H₇ | H | | |
| H | H | H | H | CH₃ | CH₃ | | |
| H | H | H | H | CH₃ | C₂H₅ | | |
| H | H | H | H | CH₃ | C₃H₇ | | |
| H | H | H | H | CH₃ | i-C₃H₇ | | |
| CH₃ | H | CH₃ | CH₃ | CH₃ | CH₃ | | |
| H | H | CH₃ | CH₃ | CH₃ | H | | |
| H | H | CH₃ | CH₃ | C₂H₅ | H | | |
| H | H | CH₃ | CH₃ | C₃H₇ | H | | |
| H | H | CH₃ | CH₃ | i-C₃H₇ | H | | |

2. n represents one

| R¹ | R² | R³ | R⁴ | R⁵ | R⁶ | R⁷ | R⁸ |
|---|---|---|---|---|---|---|---|
| H | H | H | H | H | H | H | H |
| CH₃ | H | H | H | H | H | H | H |
| H | H | CH₃ | H | H | H | H | H |
| H | H | H | H | CH₃ | H | H | H |
| C₂H₅ | H | H | H | H | H | H | H |
| H | H | C₂H₅ | H | H | H | H | H |
| H | H | H | H | C₂H₅ | H | H | H |
| n-C₃H₇ | H | H | H | H | H | H | H |
| H | H | n-C₃H₇ | H | H | H | H | H |
| H | H | H | H | n-C₃H₇ | H | H | H |
| i-C₃H₇ | H | H | H | H | H | H | H |
| H | H | i-C₃H₇ | H | H | H | H | H |
| H | H | H | H | i-C₃H₇ | H | H | H |
| t-C₄H₉ | H | H | H | H | H | H | H |
| H | H | t-C₄H₉ | H | H | H | H | H |
| H | H | H | H | t-C₄H₉ | H | H | H |
| CH₃ | CH₃ | H | H | H | H | H | H |
| CH₃ | C₂H₅ | H | H | H | H | H | H |
| CH₃ | n-C₃H₇ | H | H | H | H | H | H |
| CH₃ | i-C₃H₇ | H | H | H | H | H | H |
| C₂H₅ | C₂H₅ | H | H | H | H | H | H |
| C₂H₅ | n-C₃H₇ | H | H | H | H | H | H |
| C₂H₅ | i-C₃H₇ | H | H | H | H | H | H |
| n-C₃H₇ | i-C₃H₇ | H | H | H | H | H | H |
| H | H | CH₃ | CH₃ | H | H | H | H |
| H | H | CH₃ | C₂H₅ | H | H | H | H |
| H | H | CH₃ | C₃H₇ | H | H | H | H |
| H | H | CH₃ | i-C₃H₇ | H | H | H | H |
| H | H | C₂H₅ | C₂H₅ | H | H | H | H |
| H | H | C₂H₅ | C₃H₇ | H | H | H | H |
| H | H | C₂H₅ | i-C₃H₇ | H | H | H | H |

-continued

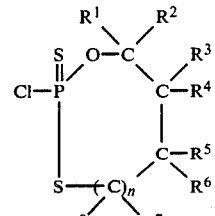

(VII)

| R¹ | R² | R³ | R⁴ | R⁵ | R⁶ | R⁷ | R⁸ |
|---|---|---|---|---|---|---|---|
| H | H | C₃H₇ | C₃H₇ | H | H | H | H |
| H | H | C₃H₇ | i-C₃H₇ | H | H | H | H |
| CH₃ | H | CH₃ | CH₃ | H | H | H | H |
| CH₃ | H | CH₃ | C₂H₅ | H | H | H | H |
| CH₃ | H | CH₃ | C₃H₇ | H | H | H | H |
| CH₃ | H | CH₃ | i-C₃H₇ | H | H | H | H |
| CH₃ | H | C₂H₅ | C₂H₅ | H | H | H | H |
| CH₃ | H | C₂H₅ | C₃H₇ | H | H | H | H |
| CH₃ | H | C₂H₅ | i-C₃H₇ | H | H | H | H |
| CH₃ | H | C₃H₇ | C₃H₇ | H | H | H | H |
| CH₃ | H | C₃H₇ | i-C₃H₇ | H | H | H | H |
| CH₃ | CH₃ | CH₃ | CH₃ | H | H | H | H |
| CH₃ | CH₃ | CH₃ | C₂H₅ | H | H | H | H |
| CH₃ | CH₃ | CH₃ | CH₃ | H | H | H | H |
| CH₃ | CH₃ | CH₃ | i-C₃H₇ | H | H | H | H |
| CH₃ | CH₃ | C₂H₅ | C₂H₅ | H | H | H | H |
| CH₃ | CH₃ | C₂H₅ | C₃H₇ | H | H | H | H |
| CH₃ | CH₃ | C₂H₅ | i-C₃H₇ | H | H | H | H |
| CH₃ | CH₃ | C₃H₇ | C₃H₇ | H | H | H | H |
| CH₃ | CH₃ | C₃H₇ | i-C₃H₇ | H | H | H | H |
| CH₃ | CH₃ | CH₃ | CH₃ | CH₃ | H | H | H |
| CH₃ | CH₃ | CH₃ | CH₃ | C₂H₅ | H | H | H |
| CH₃ | CH₃ | CH₃ | CH₃ | C₃H₇ | H | H | H |
| CH₃ | CH₃ | CH₃ | CH₃ | i-C₃H₇ | H | H | H |
| H | H | H | H | CH₃ | CH₃ | H | H |
| H | H | H | H | CH₃ | C₂H₅ | H | H |
| H | H | H | H | CH₃ | C₃H₇ | H | H |
| H | H | H | H | CH₃ | i-C₃H₇ | H | H |
| CH₃ | H | CH₃ | CH₃ | CH₃ | CH₃ | H | H |
| H | H | H | H | H | H | CH₃ | CH₃ |
| H | H | H | H | H | H | CH₃ | C₂H₅ |
| H | H | H | H | H | H | CH₃ | C₃H₇ |
| H | H | H | H | H | H | CH₃ | i-C₃H₇ |
| H | H | H | H | H | H | C₂H₅ | H |
| H | H | H | H | H | H | C₃H₇ | H |
| H | H | H | H | H | H | i-C₃H₇ | H |
| H | H | CH₃ | CH₃ | H | CH₃ | H | H |
| H | H | CH₃ | CH₃ | H | C₂H₅ | H | H |
| H | H | CH₃ | CH₃ | H | C₃H₇ | H | H |
| H | H | CH₃ | CH₃ | H | i-C₃H₇ | H | H |

Virtually all inert organic solvents are suitable as diluents for the process variants (a), (b) and (c) according to the invention and for the preparation of the new compounds of the general formula (VII). These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide, N-methylpyrrolidone, and dimethyl sulphoxide, tetramethylene sulphone and hexamethylphosphoric acid triamide.

The process variants (a), (b) and (c) according to the invention (including processes for the preparation of the compounds of the general formula (VII)) are carried out in general at temperatures between −50° C. and 120° C. The range between 0° C. and 110° C. is preferred. The reactions are carried out in general under atmospheric pressure.

The process variants (a), (b) and (c), including the processes for the preparation of the new compounds of the general formula (VII), are carried out, if appropriate, in the presence of acid acceptors. All customary acid-binding agents can be used as acid acceptors. Alkali metal carbonates and alcoholates, such as sodium carbonate and potassium carbonate, sodium methylate, potassium methylate, sodium ethylate and potassium ethylate, and aliphatic, aromatic and heterocyclic amines, for example triethylamine, trimethylamine, dimethylaniline, dimethylbenzylamine and pyridine, have proved particularly useful. As far as in carrying out the process variants according to the invention no acids are formed, the addition of acid acceptors is not required.

To carry out process variant (a) according to the invention, 1 to 1.6 mols in particular 1 to 1.4 mols, of the compounds of the general formula (III) are preferably employed per mol of (di)thiophosphor(n)ic dichloride (formula II).

To carry out process variant (b) according to the invention, 2 to 3.2 mols in particular 2 to 2.8 mols, of the compounds of the general formula (V) are preferably employed per mol of dithiophosphonic anhydride of the formula (IV).

To carry out process variant (c) according to the invention, and for the preparation of the compounds of the general formula (VII), 1 to 1.6 mols, in particular 1 to 1.4 mols, of the compounds of the general formula (III) are preferably employed per mol of thiophosphoryl trichloride. 1 to 1.6 mols, preferably 1 to 1.4 mols, of the compounds of the general formula (VIII) are employed per mol of the compounds of the general formula (VII). In the case where R represents amino, alkylamino or methyl-alkylamino and M represents hydrogen, preferably 2 to 3.2, in particular 2 to 2.8 mols, of the compounds of the general formula (VIII) are used per mol of the compounds of the general formula (VII).

Working-up is effected by customary methods, for example by extraction of the products with toluene or methylene chloride from the reaction mixture diluted with water, washing of the organic phase with water, drying and distillation or so-called "insipient distillation", that is to say prolonged heating to moderately elevated temperatures under reduced pressure in order to free them from the final volatile constituents, or by chromatographic purification over silica gel. The compounds are characterized by their refractive index, melting point, $R_f$ value or boiling point, or the $^{31}$p-NMR chemical shift.

The active compounds are well tolerated by plants, have a favorable level of toxicity to warm-blooded animals, and are suitable for combating animal pests, preferably arthropods, especially insects, arachnida and nematodes, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus*, *Armadillidium vulgare* and *Porcellio scaber*.

From the order of the Diplopoda, for example, *Blaniulus guttulatus*. From the order of the Chilopoda, for example, *Geophilus carpophagus* and *Scutigera spec.* From the order of the Symphyla, for example, *Scutigerella immaculate*. From the order of the Thysanura, for example *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria*. From the order of the Dermapters, for example, *Forficula auricularia*. From the order of the Isoptera, for example *Reticulitermes spp*. From the order of the Anoplura, for example, *Phylloxera vastatrix, Pemphigus Spp., Pediculus humanus corporis, Haematopinus spp. Linognathus spp.* From the order of the Mallophaga, for example, *Trichodectes spp.* and *Damalinea spp.* From the order of the Thysanopters, for example, *Hercinothrips femoralis* and *Thrips tabaci.* From the order of the Heteroptera, for example, *Eurygaster spp., Dysdercus intermedius, Piesma quadrata, Cimex lectularius, Rhodnius pralixus* and *Triatoma spp.* From the order of the Homoptera, for example, *Aleurodes brassicae, Bemisia tabaci, Trialeurodes vaporariorum, Aphis gossypii, Brevicoryne brassicae, Cryptomyzus ribis, goralis fabae, Doralis pomi, Eriosoma Lanigarum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia pleae, Laodelphax striatellus, Nilaparvata Lungens, Aonidiella aurantii, Aspidiotus hederae, Pseudocottus spp.* and *Psylla spp.* From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiells, Phyllocnistis citrella, Agrotis spp., Laphygma exigua, spp., Earias insulana, Heliothis spp., Laphygma exigua, Mamestra brassicae, Panolis flammea, Prodenia Litura, Spodoptera spp., Trichoplusia ni, Carpocapsa pomonella, Pieris spp., Chilo spp., Pyrausta nubitalis; Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryraephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneos, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica*. From the order of the Hymenoptera, for example, *Diprion spp., Hoplocampa spp., Lasius spp., Monomorium pharaonis* and *Vespa spp*. From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp.,*

*Bibio hortulanus, Oscinella frit, Phorbia spp., Pegomyia hyoscyami, Ceratitis capitate, Dacus oleae* and *Tipula paludosa*. From the order of the Siphon-aptera, for example, *Xenopsylla cheopis* and *Ceratophyllus spp.*. From the order of the Arachnida, for example, *Scorpio maurus* and *Latrodectus mactans*. From the order of the Acarina, for example, *Acarus siro, Argas spp., Ornithodoros spp., Dermanyssus gallinae, Eriophyes ribrs, Phyllocoptruta oleivora, Boophilus spp., Rhipicephatus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The phytoparasitic nematodes include *Pratylenchus spp., Radopholus similis, Ditylenthus dipsaci, Tylenchulus semipenetrans, Heterodera spp., Meloidogyne spp., Aphelenchoides spp., Longidorus spp., Xiphinema spp.* and *Trichodorus spp.*.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms prepared from these formulations, as a mixture with other active compounds, such as insecticides, baits, sterilizing agents, acarcides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating undesired pests, such as insects, ticks and mites, in the field of animal husbandry and animal breeding, and better results, for example higher milk yields, higher weight, better animal hide, longer life, etc., can be achieved by combating the pests.

The active compounds according to the invention are used in a known manner in these sectors, such as by external application, for example in the form of dipping, spraying and pouring on and spotting on.

The examples which follow are intended to illustrate the preparation of the substances according to the invention in more detail.

EXAMPLE 1

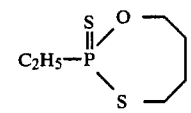

16.3 g (0.1 mol) of ethanethiophosphonic dichloride in 1 l of toluene are initially introduced, and a mixture of 11 g (0.1 mol) of 3-mercaptobutan-1-ol and 22 g (0.22 mol) of triethylamine in 100 ml of tetrahydrofuran is slowly added dropwise at 20° C. The mixture is heated at 80° C. for 2 days, and 200 ml of toluene and 200 ml of water are then added to the reaction mixture. The organic phase is separated off, washed with water and dried, and the solvent is distilled off, first under a vacuum from a waterpump and then under a high vacuum. 11.5 g (59 % of theory) of 2-ethyl-1,3,2-oxathiaphosphepane 2-sulphide having a refractive index $n_D^{20}=1.5761$ are obtained.

EXAMPLE 2

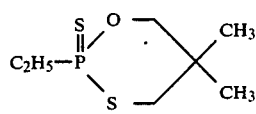

6.2 g (0.025 mol) of ethanethiophosphonic dithioanhydride are suspended in 50 ml of toluene, and a solution of 6.1 g (0.05 mol) of 3-chloro-2,2-dimethylpropanol in 20 ml of toluene is added dropwise at 50° C. The mixture is stirred for 2 hours at 20° C., and 5.6 g (0.055 mol) of triethylamine are then added dropwise to the reaction mixture. The mixture is then heated under reflux for 2 days The mixture is then heated under reflux for 2 days and cooled, 20 ml of 2N sodium hydroxide solution are then added, the organic phase is washed neutral with water and dried, and the solvent is distilled off, first under a vacuum from a water pump and then in high vacuum. 5.3 g (50% of theory) of 2-ethyl-5,5-diethyl-1,3,2-oxathiaphosphorinane 2-sulphide having a melting point of 77°–79° C. are obtained.

EXAMPLE 3

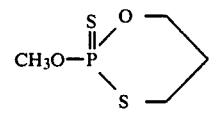

17 g (0.1 mol) of thiophosphoryl trichloride in 1 l of toluene are initially introduced, and a solution of 24 g (0.24 mol) of triethylamine and 9.3 g (0.1 mol) of 3-mercaptopropanol in 200 ml of tetrahydrofuran is added dropwise at 0° C. in the course of 2 hours. The mixture is heated to 20° C. and stirred at this temperature for 1 day. Thereafter, the reaction mixture is extracted with ice water, the organic phase is dried, and the solvent is distilled off under a vacuum from a waterpump. the crude product is further purified by filtration over about 500 g of silica gel with 3 l of mobile phase (cyclohexane:acetone (parts by volume)=10:1). When the solvent has been distilled off, 4.2 g of 2-chloro-1,3,2-oxathiaphosphorinane 2-sulphide having a refractive index $n_D^{20}=1.6178$ are obtained.

3.8 g (0.02 mol) of this chloride are dissolved in 50 ml of tetrahydrofuran, and a solution of 1.1 g of sodium methylate in 30 ml of methanol is added at 0 to 10° C. The mixture is stirred for 10 minutes, the solvent is distilled off under a vacuum from a waterpump, the residue is taken up with methylene chloride, and the solution is washed with saturated sodium chloride solution, dried and filtered over 300 g of silica gel (3 l of $CH_2Cl_2$ solution). After the solvent has been distilled off, 2.6 g of 2-methoxy-1,3,2-oxathiaphosphorinane 2-sulphide having a refractive index $n_D^{20}=1.5744$ are obtained.

The following can be obtained analogously to 15 Examples 1 to 3:

| Example No. | R | n | $R^1$ | $R^2$ | $R^3$ | $R^4$ | $R^5$ | $R^6$ | $R^7$ | $R^8$ | Physical data $(n_D^{20})$ |
|---|---|---|---|---|---|---|---|---|---|---|---|
| 4 | n-$C_3H_7$ | 1 | H | H | H | H | H | H | H | H | 1.570 |
| 5 | i-$C_3H_7$ | 1 | H | H | H | H | H | H | H | H | |
| 6 | $C_2H_5$ | 1 | $CH_3$ | H | H | H | H | H | H | H | 1.5570 |
| 7 | $C_2H_5$ | 0 | H | H | $CH_3$ | n-$C_3H_7$ | H | H | — | — | 1.5369 |
| 8 | $C_2H_5$ | 0 | H | H | n-$C_3H_7$ | $CH_3$ | H | H | — | — | 1.5327 |
| 9 | n-$C_3H_7$ | 0 | H | H | H | H | H | H | — | — | 1.5794 |
| 10 | $ClCH_2$ | 0 | H | H | H | H | H | H | — | — | 1.6305 |
| 11 | $CH_3$ | 0 | H | H | H | H | H | H | — | — | mp. 51–53° C. |
| 12 | $CH_3NH$ | 0 | H | H | H | H | H | H | — | — | 1.482 |
| 13 | $(CH_3)_2N$ | 0 | H | H | H | H | H | H | — | — | 1.5809 |
| 14 | $C_2H_5$ | 0 | H | H | H | H | H | $CH_3$ | — | — | 1.562 |
|   |   |   |   |   |   | (isomer I) |   |   |   |   |   |
| 15* | $C_2H_5$ | 0 | H | H | $CH_3$ | n-$C_3H_7$ | H | H | — | — | 1.5332 |
| 16 | $CH_3$ | 0 | H | H | H | H | H | $CH_3$ | — | — | mp. 70–72° C. |
|   |   |   |   |   |   | (isomer I) |   |   |   |   |   |
| 17 | $C_2H_5$ | 0 | H | H | H | H | H | H | — | — | 1.5908 |
| 18 | $CH_3$ | 1 | H | H | H | H | H | H | H | H | 1.5932 |
| 19 | $CH_3$ | 0 | H | H | $CH_3$ | $CH_3$ | H | H | | | mp. 66–68° C. |
| 20 | $C_2H_5$ | 0 | H | H | $C_2H_5$ | $C_2H_5$ | H | H | | | 1.554 |
| 21* | $C_2H_5$ | 0 | H |  | | | H | H | | | 1.5725 |
| 22 | $C_2H_5$ | 0 | H | H | $C_2H_5$ | $C_2H_5$ | H | H | | | |
|   |   |   |   |   |   | (isomer I) |   |   |   |   |   |
| 23 | $CH_3$ | 0 | H | H | $CH_3$ n-$C_3H_7$ | | H | H | | | 1.553 |
| 24 | $C_2H_5$ | 0 | H | i-$C_3H_7$ | $CH_3$ | $CH_3$ | H | H | | | mp. 99–100° C. |
|   |   |   |   |   |   | (isomer I) |   |   |   |   |   |

-continued

| Example No. | R | n | $R^1$ | $R^2$ | $R^3$ | $R^4$ | $R^5$ | $R^6$ | $R^7$ | $R^8$ | Physical data ($n_D^{20}$) |
|---|---|---|---|---|---|---|---|---|---|---|---|
| 25 | $C_2H_5$ | 0 | H | i-$C_3H_7$ | $CH_3$ | $CH_3$ (isomer II) | H | | | | 1.5405 |
| 26 | $CH_3$ | 0 | H | i-$C_3H_7$ | $CH_3$ | $CH_3$ (isomer I) | H | H | | | mp. 114–116° C. |
| 27 | $CH_3$ | 0 | H | i-$C_3H_7$ | $CH_3$ | $CH_3$ (isomer II) | H | H | | | 1.5375 |
| 28 | $CH_3$ | 0 | H | n-$C_3H_7$ | H | $C_2H_5$ (isomer I) | H | H | | | 1.542 |
| 29 | $CH_3$ | 0 | H | n-$C_3H_7$ | H | $C_2H_5$ (isomer II) | H | H | | | 1.5505 |
| 30 | $C_2H_5$ | 0 | H | n-$C_3H_7$ | H | $C_2H_5$ (isomer I) | H | H | | | 1.540 |
| 31 | $C_2H_5$ | 0 | H | n-$C_3H_7$ | H | $C_2H_5$ (isomer II) | H | H | | | 1.5415 |
| 32 | $CH_3$ | 0 | H | H | i-$C_3H_7$ | H | H | | | | 1.5656 |
| 33 | $CH_3$ | 0 | H | H | —$CH_2CH_2CH$=$CHCH_2$— | | H | H | | | mp. 82–83° C. |
| 34 | $CH_3$ | 0 | H | H | —$(CH_2)_5$— | | H | H | | | mp. 72–75° C. |
| 35 | $CH_3$ | 0 | H | H (isomer I) | H | —$(CH_2)_4$— | | H | | | mp. 66–68° C. |
| 36 | $CH_3$ | 0 | H | H | —$CH_2CH_2CH$=$CHCH_2$—<br>$\quad\quad\quad\quad\quad\quad\quad$ $CH_3$ | | | H | | | mp. 119–122° C. |
| 37 | $CH_3$ | 0 | H | H | $C_2H_5$ | n-$C_4H_9$ | H | H | | | 1.542 |
| 38 | $CH_3$ | 1 | H | $CH_3$ | H | H | H | H | H | H | 1.568 |
| 39 | $CH_3$ | 0 | H | | $CH_3$, $CH_3$ (cyclopropane) | | H | H | | | mp. 138–142° C. |
| 40* | $CH_3$ | 0 | H | —$CH(CH_3)CH_2CH_2CH_2$— | | H | $CH_3$ | $CH_3$ | | | 1.558 |
| 41 | $C_2H_5$ | 0 | H | —$CH(CH_3)CH_2CH_2CH_2$— (isomer I) | | H | $CH_3$ | $CH_3$ | | | 1.557 |
| 42 | $C_2H_5$ | 0 | H | —$CH(CH_3)CH_2CH_2CH_2$— (isomer II) | | H | $CH_3$ | $CH_3$ | | | 1.5575 |
| 43 | $CH_3$ | 0 | H | $CH_3$ | H | H | H | H | | | 1.579 |
| 44 | $CH_3NH$ | 0 | H | H | H | H | $CH_3$ | H | | | mp. 64–65° C. |
| 45 | $C_2H_5$ | 0 | H | H | H | H (isomer II) | $CH_3$ | H | | | 1.572 |
| 46 | $CH_3$ | 0 | H | H | H | H (isomer I) | n-$C_3H_7$ | H | | | 1.561 |
| 47 | $CH_3$ | 0 | H | H | H | H (isomer II) | n-$C_3H_7$ | H | | | 1.5565 |
| 48* | $CH_3$ | 0 | H | H | —$CH_2$—CH—CH=CH—CH—<br>$\quad\quad\quad\quad\quad\quad$ $CH_2$ | | H | H | | | 1.589 |
| 49 | $C_2H_5$ | 0 | H | H | H | H (isomer I) | n-$C_3H_7$ | H | | | 1.5465 |
| 50 | $C_2H_5$ | 0 | H | | H | H (isomer II) | n-$C_3H_7$ | H | | | 1.5565 |
| 51 | $CH_3$ | 0 | H | H | H | —$CH_2CH_2CH_2CH_2$— | | H | | | 1.540 |
| 52 | $CH_3O$ | 0 | H | H | | H | n-$C_3H_7$ | H | | | |
| 53 | $CH_3$ | 0 | H | H | $CH_3$ | H | $CH_3$ | H | | | |
| 54 | $CH_3$ | 0 | H | H | H | H (isomer I) | n-$C_4H_9$ | H | | | 1.5385 |
| 55 | $CH_3$ | 0 | H | H | H | H (isomer II) | n-$C_4H_9$ | H | | | 1.5520 |
| 56 | $CH_3$ | 0 | H | H | H | H | $CH_3$ | $CH_3$ | | | |
| 57 | $C_2H_5$ | 0 | H | H | H | H | $CH_3$ | $CH_3$ | | | 1.5585 |
| 58 | $CH_3$ | 0 | H | H | H | H | $C_2H_5$ | H | | | |
| 59 | $CH_3$ | 0 | H | H | H | H (isomer II) | $CH_3$ | H | | | mp. 63–65° C. |
| 60 | $CH_3$ | 0 | H | H | $C_2H_5$ | $C_2H_5$ | H | H | | | mp. 53–55° C. |

According to part 1 of Example 3 the following compound of formula VII is obtained:

| | | 0 | H | H | H | H | | n-$C_3H_7$ | H | | | 1.5755 |

*isomer mixture

The examples which follow are intended to illustrate the biological activity of the new compounds of the general formula (I). In some tests, the compound of the formula

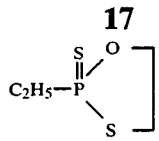

disclosed in German Patent Specification No. 1,104,520 was employed.

EXAMPLE A

LD$_{100}$ test
Test insects: *Leucophaea maderae*
Number of insects: 5
Solvent: acetone 2 parts by weight of active compound are taken up in 1,000 parts by volume of the solvent. The solution thus obtained is diluted with further solvent to the desired concentrations.

2.5 ml of the solution of active compounds are pipetted into a Petri dish. On the bottom of the Petri dish there is a filter paper with a diameter of about 9.5 cm. The petri dish remains uncovered until the solvent has completely evaporated. The amount of active compound per m$^3$ of filter paper varies with the concentration of the solution of active compound. The stated number of test insects is then placed in the Petri dish and the dish is covered with a glass lid.

The condition of the test insects is checked 3 days after the commencement of the experiments. The destruction in % is determined. 100% means that all the test insects have been killed; 0% means that none of the test insects have been killed.

In this test, for example, the compounds from the preparation Examples 1, 2 and 3 showed 100% destruction at an active compound concentration of 0.2%.

EXAMPLES 8

Test insect: *Phorbia antiqua* grubs (in the soil)
Solvent: 3 parts by weight of acetone
Emulsifer: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practially no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of preparation Examples 1, 2, 3, 4, 5, 6, 7, 8, 9, 11, 15 and 17 no destruction (0%) at the same concentration.

EXAMPLE C

Test insect; *Diabrotica balteata* larvae (in the soil)
Solvent: 3 parts by weight of acetone
Emulsifer: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined determined ion % by counting the dead and live test insects. The degree of effectiveness is 100% if all the test insects have been killed and is 0% if just as many test insects are still alive as in the case of the untreated control.

In this test, for example, the compounds of preparation Examples 1, 2, 3, 4, 6, 7, 8, 9, 11, 12, 15 and 17 showed 100% destruction at an active compound concentration of 20 ppm, whereas the comparative compound (A) gave no destruction (0%) at the same concentration.

EXAMPLE D

LT$_{100}$ test for Diptera
Test insects: *Musca domestica*
Number of test insects: 25
Solvent: acetone 2 parts by weight of active compound are taken up in 1,000 parts by volume of solvent. The solution thus obtained is diluted with further solvent to the desired lower concentrations.

2.5 ml of the solution of active compound are pipetted into a Petri dish. On the bottom of the Petri dish there is a filter paper with a diameter of about 9.5 cm. The Petri dish remains uncovered until the solvent has completely evaporated. The amount of active compound per m$^3$ of filter paper varies with the concentration of the solution of active compound used. The stated number of test insects is then placed in the Petri dish and the dis is covered with a glass lid.

The condition of the test insects is continously checked. The time which is necessary for a 100% knock-down effect (LT$_{100}$) is determined.

In this test, for example at an active compound concentration of 0.002%, the LT$_{100}$ was reached after no longer than 360 minutes by the compounds from the preparation Examples 1, 3, 4, 6, 9, 11, 14, 15 and 16, whereas in the case of the comparative compound (A) at the same concentration the LT$_{100}$ was not reached after 360 minutes (0%).

EXAMPLE E

Test with *Lucilia cuprina* resistant Larvae
Solvent:
　35 parts by weight of ethylene glycol monomethyl ether
　35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. Larvae are introduced into a test tube which contains approx. 1 cm³ of horse muscle and 0.5 ml of the preparation of active compound. After 24 hours, the degree of destruction is determined.

In this test, for example, the compounds from the preparation Examples 1, 4, 11, 15 and 17 showed a degree of destruction of 100% at an active compound concentration of 300 ppm.

EXAMPLE F $LD_{100}$ test
Test insects: *Sitophulus granarius*
Number of test insects: 25
Solvent: acetone 2 parts by weight of active compound are taken up in 1,000 parts by volume of the solvent. The solution thus obtained is diluted with further solvent to the desired concentrations.

2.5 ml of the solution of active compound are pipetted into a Petri dish. On the bottom of the Petri dish there is a filter paper with a diameter of about 9.5 cm. The Petri dish remains uncovered until the solvent has completely evaporated. The amount of active compound per m³ of filter paper varies with the concentration of the solution of active compound. The stated number of test insects is then placed in the Petri dish and the dish is covered with a glass lid.

The condition of the test insects is checked 3 days after the commencement of the experiments. The destruction in % is determined. 100% means that all the test insects have been killed; 0% means that none of the test insects have been killed.

In this test, for example, the compounds of Examples 4, 14, 15 and 16 showed 100% destruction at a concentration of 0.02, whereas the comparative compound (A) gave only 60% destruction at the same concentration.

EXAMPLE G

Laphygma test
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amound of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as Long as the leaves are still moist.

After the specified period of time, the destruction in % is determined. 100% means that all the caterpillars have been killed; 0% means that none of the caterpillars have been killed.

In this test, for example, the compounds of preparatio Examples 1, 3, 4, 7, 11, 12, 14 and 15 showed 100% destruction at an active compound concentration of 0.01%, whereas the comparative compound (A) gave no destruction (0%) at the same concentration.

EXAMPLE H

Doralis test (systemic action)
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which have been heavily infested with the bean aphid (*Doralis fabae*) are each watered with 20 ml of the preparation of the active compound of the desired concentration in such a way that the preparation of the active compound penetrates into the soil without wetting the shoot. The active compound is taken up by the roots and passes to the shoot.

After the specified period of time, the destruction in % is determined. 100% means that all the aphids have been killed; 0% means that none of the aphids have been killed.

In this test, for example, the compounds of preparation Examples 3, 11, 12, and 17 showed 10% destruction at an active compound concentration of 0.01%, whereas the comparative compound (A) gave no destruction (0%) at the same concentration.

EXAMPLE J

Critical concentration test / root-systemic action
Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the compounds of preparation Examples 1, 12 and 17 showed a 100% effect at an active compound concentration of 20 ppm, whereas the comparative compound (A) gave no destruction (0%) at the same concentration.

EXAMPLE K

Critical concentration test / root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deducted from the mortality figures. It is 100% if all the test insects have been killed and 0% if just as many test insects are still alive as in the case of the untreated control.

In this test, for example, the compounds of preparation Examples 1, 9, 12, 13 and 17 showed 100% destruction at an active compound concentration of 20 ppm, whereas the comparative compound (A) gave no destruction (0%) at the same concentration.

EXAMPLE L

Critical concentration test/nematodes
Test nematode: *Meloidogyne incognite*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the Lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds of preparation Examples 1, 4, 6, 7, 8, 9, 15 and 17 showed a degree of effectiveness of 100% at an active compound concentration of 20 ppm, whereas the comparative compound (A) gave a degree of effectiveness of 0% at the same concentration.

EXAMPLE M

Critical concentration test/nematodes
Test nematode: *Globodera rostochiensis*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, potatoes are planted and the pots are kept at a greenhouse temperature of 18° C.

After six weeks, the potato roots are examined for cysts, and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds of preparation Examples 1 and 17 showed a degree of effectiveness of 100% at an active compound concentration of 20 ppm, whereas the comparative compound (A) gave a degree of effectiveness of 0% at the same concentration.

It will be understood that the specification and examples are illustrative but not limitative of the present invention and that other embodiments within the spirit and scope of the invention will suggest themselves to those skilled in the art.

We claim:

1. A phosphorus-containing heterocycle of the formula

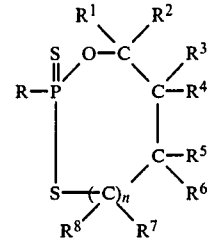

in which

R represents amino, $C_1$–$C_6$-alkylamino, methyl-($C_1$–$C_6$-alkyl)-amino or optionally halogen-substituted $C_1$–$C_6$-alkylthio, $C_1$–$C_6$-alkoxy or $C_1$–$C_6$-alkylthio, $R^1$ to $R^8$ are identical or different and represent hydrogen, halogen, $NO_2$, $C_1$–$C_6$-alkyl which can be halogen-substituted, $C_2$–$C_8$-alkenyl, di-($C_1$–$C_4$-alkyl)-amino, $C_1$–$C_4$-alkoxy-$C_1$–$C_4$-alkyl, $C_1$-alkylthio-$C_1$–$C_4$-alkyl, benzyl or phenyl, or in which two of the radicals $R^1$ to $R^8$, together with the carbon atom or carbon atoms to which they are bonded, form a $C_5$–$C_7$-cycloalkyl or cycloalkenyl ring which can be substituted by methyl or ethyl and which can be bridged by a methylene or ethylene group to form a bicyclic ring, and n represents zero or one.

2. A compound according to claim 1 in which

R represents $C_1$–$C_4$-alkyl, $C_1$–$C_6$-alkoxy, $C_1$–$C_4$-alkylthio, $C_1$–$C_4$-alkylamino or methyl-($C_1$–$C_4$-alkyl)-amino, $R^1$ to $R^8$ are identical or different and represent hydrogen, nitro, or optionally halogen-substituted $C_1$–$C_4$-alkyl, or represent $C_1$–$C_4$-alkylthio-$C_1$–$C_4$-alkyl, or two of the radicals $R^1$ to $R^8$, together with the carbon atoms to which they are bonded, form a 5-membered or 6-membered cycloalkyl or cycloalkenyl ring which can be bridged by a methylene or ethylene group to form a bicyclic ring, and n represents zero or one.

3. A compound according to claim 1, wherein such compound is 2-ethyl-1,3,2-oxathiaphosphepane 2-sulphide of the formula

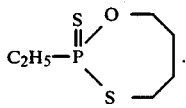

4. A compound according to claim 1, wherein such compound is 2-methyl-1,3,2-oxathiaphosphorinane 2-sulphide of the formula

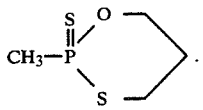

5. A compound according to claim 1, wherein such compound is 2-ethyl-4-methyl-1,3,2-oxathiaphosphorinane 2-sulphide of the formula

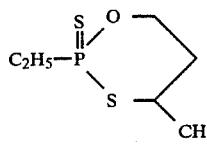

6. A compound according to claim 1, wherein such compound is 2,4-dimethyl-1,3,2-oxathiaphosphorinane 2-sulphide of the formula

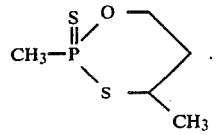

7. A compound according to claim 1, wherein such compound is 2-ethyl-4,4-dimethyl-1,3,2-oxathiaphosphorinane 2-sulphide of the formula

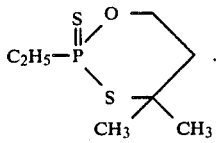

8. An arthropodicidal composition comprising an arthropodicidally effective amount of a compound according to claim 1 in admixture with a diluent.

9. A method of combatting arthropods which comprises applying to such arthropods or to an arthropod habitat an arthropodicidally effective amount of a compound according to claim 1 in admixture with a diluent.

10. The method according to claim 9, wherein such compound is 2-ethyl-1,3,2-oxathiaphosphepane 2-sulphide,
2-methyl-1,3,2,-oxathiaphosphorinane 2-sulphide,
2-ethyl-4-methyl-1,3,2-oxathiaphosphorinane 2-sulphide,
2,4-dimethyl-1,3,2-oxathiaphosphorinane 2-sulphide or
2-ethyl-4,4-dimethyl-1,3,2-oxathiaphosphorinane 2-sulphide

* * * * *

UNITED STATES PATENT AND TRADEMARK OFFICE
CERTIFICATE OF CORRECTION

PATENT NO. : 4,695,563    Page 1 of 3
DATED : Sept. 22, 1987
INVENTOR(S) : Krüger et al.

It is certified that error appears in the above-identified patent and that said Letters Patent is hereby corrected as shown below:

| | |
|---|---|
| Col. 1, line 41 | Delete "$R^5$" and substitute --$R^8$-- |
| Col. 1, line 42 | Correct spelling of --halogen-- |
| Col. 3, line 37 | Correct spelling of --i.-propyl-- |
| Col. 3, line 37 | Insert --.-- after "n" and "i" in the second instance |
| Col. 3, line 52 | Correct spelling of --propylthio-- |
| Col. 3, line 55 | Delete "$R_8$" and substitute --$R^8$-- |
| Col. 4, line 56 | Delete "alkenyloxy" and substitute --alkylthio-- |
| Col. 4, line 60 | Correct spelling of --alkylthio-- |
| Col. 5, line 32 | Correct spelling of --dimethylamino-- |
| Col. 6, line 33 | Insert --general formula (VII):-- at end of sentence |
| Col. 10, line 12 | Correct spelling of --Dermaptera-- |
| Col. 10, line 19 | Correct spelling of --Thysanoptera-- |
| Col. 10, line 27 | Correct spelling of --Doralis-- |
| Col. 10, line 27 | Correct spelling of --Lanigerum-- |
| Col. 10, line 31 | Correct spelling of --oleae-- |
| Col. 10, line 32 | Correct spelling of --Pseudococcus-- |
| Col. 10, line 38 | Correct spelling of --thurberiella-- |
| Col. 10, line 39 | Delete "Laphygma exigua" and substitute --Euxoa spp., Feltia-- |
| Col. 10, line 53 | Correct spelling of --Oryzaephilus-- |
| Col. 10, line 57 | Correct spelling of --aeneus-- |
| Col. 11, line 2 | Correct spelling of --capitata-- |
| Col. 11, line 9 | Correct spelling of --Rhipicephalus-- |
| Col. 11, line 14 | Correct spelling of --Ditylenchus-- |
| Col. 12, line 22 | Correct spelling of --acaricides-- |

UNITED STATES PATENT AND TRADEMARK OFFICE
CERTIFICATE OF CORRECTION

PATENT NO. : 4,695,563  Page 2 of 3
DATED : Sept. 22, 1987
INVENTOR(S) : Krüger et al.

It is certified that error appears in the above-identified patent and that said Letters Patent is hereby corrected as shown below:

| | |
|---|---|
| Col. 13, line 28 | Delete "The mixture is then heated under reflux for 2 days" in the first instance |
| Col. 15, Example 25 | Insert --H-- under Col. $R^6$ |
| Col. 15, Example 32 | Insert --H-- under Col. $R^6$ |
| Col. 15, Example 50 | Insert --H-- under Col. $R^2$ |
| Col. 15, Example 52 | Insert --H-- under Col. $R^3$ |
| Col. 17, line 60 | Insert --12,-- after "11" |
| Col. 17, line 60 | Insert after "17" --showed 100% destruction at an active compound concentration of 20 ppm, whereas the comparative compound (A) gave-- |
| Col. 18, line 14 | Delete "determined ion" and insert --in-- |
| Col. 18, line 44 | Delete "dis" and insert --dish-- |
| Col. 19, line 47 | Correct spelling of --amount-- |
| Col. 19, line 58 | Correct spelling of --preparation-- |
| Col. 21, line 18 | Correct spelling of --deduced-- |

UNITED STATES PATENT AND TRADEMARK OFFICE
CERTIFICATE OF CORRECTION

PATENT NO. : 4,695,563

DATED : Sept. 22, 1987

INVENTOR(S) : Krüger et al.

It is certified that error appears in the above-identified patent and that said Letters Patent is hereby corrected as shown below:

Col. 21, line 30    Correct spelling of --incognita--

Col. 22, line 47    Delete "alkylthio" in the first instance and substitute --alkyl--

Col. 22, line 51    Insert --$C_4$-- between "$C_1$" and "alkylthio"

Signed and Sealed this

Thirty-first Day of May, 1988

Attest:

DONALD J. QUIGG

Attesting Officer

Commissioner of Patents and Trademarks